United States Patent [19]
Arffmann et al.

[11] Patent Number: 5,895,787
[45] Date of Patent: Apr. 20, 1999

[54] TREATMENT OF FIBROMYALGIA AND RELATED DISORDERS

[75] Inventors: Kathleen Arffmann, New York City, N.Y.; G. Merrill Andrus, Orem, Utah

[73] Assignee: Designed Nutritional Products, Inc., Vineyard, Utah

[21] Appl. No.: 08/954,995

[22] Filed: Oct. 8, 1997

[51] Int. Cl.$^6$ .................................................. A61K 31/405
[52] U.S. Cl. ................................................................ 514/415
[58] Field of Search ................................................. 514/415

[56] References Cited

U.S. PATENT DOCUMENTS

| | | | |
|---|---|---|---|
| 4,428,962 | 1/1984 | Bristol et al. | 514/415 |
| 4,877,798 | 10/1989 | Sorensen | 514/317 |
| 5,314,908 | 5/1994 | McAfee | 514/415 |
| 5,641,800 | 6/1997 | Bach et al. | 514/415 |
| 5,707,642 | 1/1998 | Yue | 514/12 |

OTHER PUBLICATIONS

Bennett, Robert, "Fibromyalgia and the Disability Dilemma", *Arthritis & Rheumatism*, vol. 39, No. 10, pp. 1627–1634, Oct. 1996.
Carette, Simon, "Fibromyalgia 20 years later: What Have We Really Accomplished?", *The Journal of Rheumatology*, 22:4, pp. 590–594, 1995.
Designed Nutritional Products, "Product Information", 1 sheet, Mar. 1, 1997.
Hadler, Nortin M., "If You Have to Prove You Are Ill, You Can't Get Well", *Spine*, vol. 21, No. 20, pp. 2397–2400, 1996.
Life Plus Foundation, "Relief From Chronic Fatigue Syndrome", Internet web site information, 7 pages, Jul. 9, 1997.
Michnovicz et al., "Changes in Levels of Urinary Estrogen Metabolites After Oral Indole–3–Carbinol Treatment in Humans", *Journal of the National Cancer Institute*, vol. 89, No. 10, pp. 718–723, May 21, 1997.
Michnovicz et al., "Dietary Cytochrome P–450 Modifiers in the Control of Estrogen Metabolism", *Food Phytochemicals I: Fruits and Vegetables*, pp. 282–293.
Nye, David A., "Fibromyaigia — a guide for patients", *Sapient Health Network*, 7 pages, Aug. 13, 1995.
Nye, David A., "Fibromyaigia — A Physician's Guide", *Sapient Health Network*, 9 pages, 1995.
Physical Medicine Research Foundation, "The Fibromyalgia Syndrome: A Consensus Report on Fibromyalgia and Disability", *The Journal of Rheumatology*, 23:3, pp. 534–539, 1996.
Romano et al., "Fibromyalgia 20 Years Later: What We Really Accomplished?", *The Journal of Rheumatology*, 23:1, pp. 192–194, 1996.
Thrive @ the healthy living experience, "Chronic Pain", 6 pages, 1996.
Wolfe et al., "Aspects of Fibromyalgia in the General Population: Sex, Pain Threshold, and Fibromyalgia Symptoms", *The Journal of Rheumatology*, 22:1, pp. 151–156, 1995.
Wolfe, Frederick, "Fibrositis, Fibromyalgia, and Musculoskeletal Disease: The Current Status of the Fibrositis Syndrome", *Arch Phys Med Rehabil*, vol. 69, pp. 527–531, Jul. 1988.
Wolfe et al., "The Prevalence and Characteristics of Fibromyalgia in the General Population", *Arthritis & Rheumatism*, vol. 38, No. 1, pp. 19–28, Jan. 1995.
Wolfe, Frederick, "When To Diagnose Fibromyalgia", *Diagnostic Issues*, vol. 20, No. 2, pp. 485–501, May 1994.

*Primary Examiner*—James H. Reamer
*Attorney, Agent, or Firm*—Trask, Britt & Rossa

[57] ABSTRACT

A method of treating fibromyalgia-like complaints (i.e., fibromyalgia, chronic fatigue syndrome and irritable bowel syndrome) in a patient, the method comprising: administering to the patient an 1H-indole-3-methanol compound (e.g., 1H-indole-3-methanol, ascorbigen, bis(3-indolyl) methane, indolo[3,2-b(carbazole)], 2-(indol-3-ylmethyl)-3,3'-diindolylmethane, 5,6,11,12,17,18-hexahydrocyclonona[, 1,2-b;4,5-b';7,8-b"]triindole, 1H-indol-3-yl methoxy methane, ethoxy 1H-indol-3-yl ethoxy methane, other ethers of 1H-indole-3-methanol) in a medically acceptable manner in a pharmaceutically effective amount on a regular basis. It has been found that the administration of such indoles, particularly, 1H-indole-3-methanol, greatly mitigates the most severe symptoms of fibromyalgia. Patients with fibromyalgia have reported a decrease in pain, less fatigue, improved sleep patterns, and an improved sense of well being resulting from the oral administration of pharmaceutically effective amounts of an 1H-indole-3-methanol compound each day.

21 Claims, No Drawings

TREATMENT OF FIBROMYALGIA AND RELATED DISORDERS

TECHNICAL FIELD

This invention generally relates to the use of various naturally occurring compounds to treat a disease, and, more particularly, to the use of the natural product indole-3-methanol and related compounds to alleviate the symptoms of fibromyalgia and related disorders.

BACKGROUND

Fibromyalgia generally is understood as a condition including widespread chronic muscle pain, fatigue, and abnormal sleep patterns. See, e.g., Wolfe et al., "The Fibromyalgia Syndrome: A Consensus Report on Fibromyalgia and Disability", *The Journal of Rheumatology*, 23(3) :534–539 (1996). It afflicts perhaps 2% of the population of the United States. Fibromyalgia varies in its effects on those who suffer from it, but in severe cases, it is completely debilitating. Fibromyalgia is closely related to chronic fatigue and irritable bowel syndromes, and some believe that these are all just different facets of the same underlying disorder. Women are 10 to 20 times more likely to get fibromyalgia than men.

Fibromyalgia signs and symptoms include: widespread pain (97.6% of the patients), tenderness in >11/18 "tender points" (90.1%), fatigue (81.4%), morning stiffness (77.0%), sleep disturbance (74.6%), parethesias (62.8%), headache (52.8%), anxiety (47.8%), dysmenorrhea (40.6%), sicca symptoms (35.8%), depression (31.5%), irritable bowel syndrome (29.6%), urinary urgency (26.3%), and Raynaud's phenomenon (16.7%).

The cause of fibromyalgia is unknown and it is difficult to diagnose accurately. Sufferers have been especially distressed by health service providers and researchers who claim the condition is psychosomatic. The disease is associated with a lack of restful sleep, although researchers have not been able to establish whether this insomnia is a cause or an effect of fibromyalgia.

No known cure exists for fibromyalgia, and elimination of the symptoms is difficult. Some help has been realized by treating those suffering with the disease with antidepressants, analgesics, gentle and controlled exercise, counseling and education, and life-style changes. Since no single one of these therapies or any combination of them has been shown to give general relief, the search continues for some treatment which will help fibromyalgia sufferers to ameliorate their symptoms. Drug treatments which have been tried include: trazodone, diphenhydramine, cyclobenzaprine, alprazolam, carisoprodol, 5-hydroxytryptophan, and amitriptyline. Pharmaceutically effective amounts of these compounds are well-known to those of skill in the art. Dietary supplements reported to reduce the symptoms of fibromyalgia include proanthocyanins, blue-green algae, malic acid and magnesium salts. It is unknown whether any of these are effective, although their usually administered dosages (which are to be considered "pharmaceutically effective amounts" for use herein) are known to those of skill in the art.

It would be a significant improvement in the art to have a treatment effective in ameliorating the symptoms of fibromyalgia syndrome (i.e., fibromyalgia, chronic fatigue syndrome and irritable bowel syndrome) or to prevent their occurrence in the first place.

1H-indole-3-methanol (CAS Registry Number [700–06–1]) is a naturally occurring product which is derived from cruciferous vegetables. It is known to exhibit substantial effects in the metabolism of estradiol as reported by many workers, and has been implicated as having potential utility in the treatment of breast cancer. In this regard, one of 1H-indole-3-methanol's pharmacological activities is that of an estradiol 2-hydroxylase inducer. Some of its effects have been summarized in a review by Michnovicz and co-workers. Michnovicz et al. "Changes in Levels of Urinary Estrogen Metabolites After Oral Indole-3-Carbinol Treatment in Humans", *J. Nat'l Cancer Inst.*, 89(10):718–23 (1997). It has also been observed that 1H-indole-3-methanol reacts with itself in stomach acid and under other conditions such as heat, light and even plain water solutions to form new compounds ("1H-indole-3-methanol compounds"). See, e.g., Michnovicz & Bradlow, "Dietary Cytochrome P-450 Modifiers in the Control of Estrogen Metabolism", *Food Phytochemicals or Cancer Prevention I, Fruits & Vegetables*, pp. 282–293, nn. 89–93, edited by Mou-Tuan et al. ACS Symposium Series 546 (American Chemical Society, Washington, D.C., 1994). Some of these 1H-indole-3-methanol compounds (e.g., diindolylmethane and indolo (3,2-b)carbazole) are reported to bind the same receptors as the 1H-indole-3-methanol. Id.

Although described for the potential treatment of breast cancer, heretofore the use of 1H-indole-3-methanol compounds for treating conditions such as fibromyalgia syndrome is not believed to have been described.

DISCLOSURE OF THE INVENTION

Dietary indoles, particularly 1H-indole-3-methanol, have now been found to greatly mitigate the most severe symptoms of fibromyalgia. Patients with fibromyalgia have reported a decrease in pain, less fatigue, improved sleep patterns, and an improved sense of well being resulting from the oral administration of pharmaceutically effective amounts of dietary indoles dervived from 1H-indole-3-methanol each day. Positive results were sometimes seen within 24 hours, and most often within 1 week after starting daily doses of the indole compound.

The invention thus includes a method of treating fibromyalgia syndrome in a patient believed to be suffering therefrom, the method comprising: administering to the patient an 1H-indole-3-methanol compound in a medically acceptable manner in a pharmaceutically effective amount on a regular basis. The invention also includes a method of making a pharmaceutical composition containing an 1H-indole-3-methanol compound or compounds for use in the treatment of fibromyalgia or a related disorder.

BEST MODE OF THE INVENTION 1H-indole-3-methanol compounds are naturally occurring compounds. These dietary indoles result from the maceration of cruciferous vegetables by the manner briefly described herein. Glucosinolates, a set of compounds containing a glucose component, a sulfur-carbon-nitrogen component, and a variable component, occur in varying ratios in varietals, leaves, stocks, stems, flowers, seeds, and roots of the brassica (or crucifiers) plants. In one glucosinolate, glucobrassicin, the variable component is 3-indolylmethyl. When the cell walls of the plant are destroyed through chopping, grinding, chewing, for example, an enzyme, myrosinase, is released. Myrosinase aids in the hydrolysis of glucobrassicin resulting in the release of 1H-indole-3-methanol, often called indole-3carbinol. 1H-indole-3-methanol is produced in sufficient quantity that it can be isolated from the juices of many of the cruciferous vegetables such as, for example, cabbage, Brussels' sprouts, or broccoli. It has also been shown that 1H-indole-3-methanol can be produced from indole by any of a number of chemical transformations.

Whether derived from the juices of cruciferous vegetables or prepared by one of a number of controlled chemical transformations, 1H-indole-3-methanol is a very reactive molecule, unless it is kept cool, dry, and isolated from species with which it easily reacts. 1H-indole-3-methanol is especially reactive with hydroxyl groups.

1H-indole-3-methanol will react with ascorbic acid to give "ascorbigen", so named because it was once thought to be the origin of ascorbic acid (vitamin C) in cruciferous vegetables. Later studies showed that vegetable juice showed a decrease in ascorbic acid upon standing due to the combination of ascorbic acid with 1H-indole-3-methanol. As previously indicated, 1H-indole-3-methanol has been studied extensively in connection with cancer prevention. It is also used as a dietary supplement to aid in the inhibition of laryngeal papillomatosis.

Numerous studies have shown that three other compounds: a carbazole, namely, indolo[2,3, -b(carbazole)], a "dimer", bis(3-indolyl) methane, a linear "trimer," namely 2-(indol-3-ylmethyl)-3,3'-diindolylmethane, and a cyclic "trimer," namely 5,6,11,12,17,18, hexahydrocyclohnona[1, 2-b;4,5-b';7,8-also result from the reactions of 1H-indole-3-methanol with itself. These four additional identified products are only a sampling of the products realized by heating 1H-indole-3-methanol.

It has been shown that the same array of products results from subjecting the 1H-indole-3-methanol to stomach acid, or even plain acidified water. Consequently, numerous workers have concluded that the mixture of dietary indoles (the "tH-indole-3-methanol compounds"), not just 1H-indole-3-methanol, is responsible for the beneficial effects seen in providing animals and humans with dietary indoles. In fact, cell tissue studies have led workers to conclude that 1H-indole-3-methanol may not be beneficial at the cell level, but that some other derivative, such as the "dimer," the "trimers," the carbazole, and/or perhaps other compound(s) in the dietary indole mixture is/are the actual entity/entities giving beneficial results.

Whether 1H-indole-3-methanol is derived from the extraction of juices of cruciferous vegetables or is prepared by a chemical transformation in which indole is a starting material, it will give the same results when ingested by humans. Since 1H-indole-3-methanol is reactive, and positive results are obtained in other applications with the reaction products of 1H-indole-3-methanol, it is believed that not only 1H-indole-3-methanol, but its reaction products will be effective in mitigating the symptoms of fibromyalgia syndrome. This family of indole containing compounds including 1H-indole-3-methanol and products derived from the reaction of 1H-indole-3-methanol with itself are called dietary indoles. The reactive nature of 1H-indole-3-methanol is an important consideration in this invention.

Preferably, the 1H-indole-3-methanol compound used to practice the invention is selected from the group consisting of 1H-indole-3-methanol, ascorbigen, (3-indolyl) methane, indolo[3,2-b(carbazole)], 2-(indol-3-ylmethyl)-3,3'-diindolylmethane, 5,6,11,12,17,18-hexahydrocyclonona[1, 2-b;4,5-b';7,8-b"]triindole, 1H-indol-3-yl methoxy methane, ethoxy 1H-indol-3-yl ethoxy methane, other ethers of 1H-indole-3-methanol, and mixtures of any thereof.

Once the 1H-indole-3-methanol compound or compounds has been chosen, methods and compositions for making dosage units containing the compounds are well-known to those of skill in the art. For instance, conventional techniques for making tablets and pills containing active ingredients are described in the standard reference, Chase et al., *Remington's Pharmaceutical Sciences*, (16$^{th}$ ed., Mack Publishing Co., Easton, Pa., USA, 1980) ("Remington's") at pages 1553 through 1584. Conventional techniques for making powders, and their composition are described at pages 1535 through 1552 of Remington's. Conventional techniques for coating pharmaceutical dosage forms are described at pages 1585 to 1593 of Remington's.

For making dosage units, e.g., tablets or capsules, the use of conventional additives, e.g., fillers, colorants, binders, and the like is contemplated. In general, any pharmaceutically acceptable additive which does not interfere with the function of the active compound can be used in the compositions.

Suitable carriers with which the compositions can be administered include lactose, starch, cellulose derivatives and the like used in suitable amounts. Mixtures of carriers can also be used.

A process of manufacturing a composition for oral administration of the invention includes mixing predetermined quantities of the active ingredient with predetermined quantities of excipients and converting the mixture into dosage units containing, for example, 5 to 1000 milligrams ("mg"), preferably 200 to 400 mg, of active ingredient.

Converting the mixture into dosage units generally involves molding the mixture into a tablet, fig a capsule with a dry mixture, or filling a capsule with a wet mixture.

Once made, the dosage units may be administered daily or several times a day to achieve the desired total dosage (e.g., every 6, 8 or 12 hours).

Although generally less desirable from a patient acceptability view point, the active ingredient may alternatively be parenterally administered in dosages equivalent to the oral dosages described herein (taking into consideration effects such as bioavailability), such as by injection or transdermal delivery.

The invention is further explained by the following illustrative examples.

EXAMPLES

Example I

Relatively pure 1H-indole-3-methanol (I3C™ from Designed Nutritional Products, Orem, UT, US) in a water solution was prepared for HPLC analysis. One sample was diluted with water and the other was diluted with methanol. By the time the partial methanol solution could be injected into the HPLC, the reaction with methanol had taken place to form 1H-indol-3-yl methoxy methane, the methyl ether of 1H-indole-3-methanol, and two peaks of about the same magnitude were observed. The same solution when diluted with water showed only one peak.

Example II

In the course of manufacturing and formulating dietary supplements containing 1H-indole-3methanol, it was observed that the carbinol in the three position is extremely reactive. In the presence of sunlight, the compound will change color in just a few hours. Upon heating at 60° C., 99% of the present 1H-indole-3-methanol will disappear from HPLC chromatograms in the course of heating, being replaced by as many as 40 or 50 different derived compounds, virtually all of them identified as containing an indole component. More detailed studies have shown that one of the first compounds to appear in a sample of 1H-indole-3-methanol undergoing heat treatment is bis (3-indolyl) methane, a "dimer" of 1H-indole-3-methanol.

Example III

Capsules containing 100 to 300 mg of 1H-indole-3-methanol (e.g., 120 mg, 200 mg, and 300 mg) were made by placing that amount of 1H-indole-3-methanol into gelatin capsules.

Example IV

Capsules containing 100 to 300 mg of bis(3-indolyl) methane were made by placing that amount of compound into gelatin capsules.

Example V

Capsules containing 100 to 300 mg of 1H-indol-3-yl methoxy methane were made by placing that amount of compound into gelatin capsules.

Example VI

Capsules containing 100 to 300 mg of ascorbigen are made by placing that amount of compound into gelatin capsules.

Example VII

Capsules containing 200 mg of 1H-indole-3-methanol (I3C™ from Designed Nutritional Products, Orem, UT, US) were made by placing that amount of 1H-indole-3-methanol into gelatin capsules.

Example VIII

K. was included in a study of the effect of dietary supplementation (300 milligrams per day of 1H-indole-3-methanol) on estrogen metabolism. K. noticed that her severe fibromyalgia symptoms and associated chronic fatigue syndrome subsided while taking the 1H-indole3-methanol. When the study was completed and she was no longer taking 1H-indole-3-methanol, her fibromyalgia syndrome (in this case, fibromyalgia and chronic fatigue) returned. She sought out a source for 1H-indole-3-methanol and began taking it again with a similar effect on her fibromyalgia symptoms.

Example IX

G. suffered from severe symptoms of fibromyalgia and chronic fatigue as well as arthritis. The first time she took the capsules of EXAMPLE m (200 mg of 1H-indole-3-methanol) in the evening, she was able to sleep 10½ hours, whereas she previously had difficulty sleeping due to the fibromyalgia pain. In subsequent days, she increased her dosage to 400 mg per day, and within a week her fibromyalgia pain was gone, although her arthritic pain remained. After about two weeks, G. found that she could tolerate her daytime fibromyalgia pain, but that 200 mg at bedtime was necessary for her to get a good night's sleep.

Example X 1H-indole-3-methanol was given to twenty-one patients suffering from fibromyalgia. Fifteen of these patients reported some positive reduction of fibromyalgia symptoms after ten days to two months. Of the twenty-one patients, six unfortunately perceived no benefit from the 1H-indole-3-methanol.

Although the invention has been described with regard to certain preferred embodiments and examples, the scope of the invention is to be defined by the appended claims.

what is claimed is:

1. A method of treating fibromyalgia syndrome in a subject believed to be suffering therefrom, said method comprising:
administering to the subject an 1H-indole-3-methanol compound in a medically acceptable manner in a pharmaceutically effective amount on a regular basis.

2. A method according to claim 1 wherein the 1H-indole-3-methanol compound is selected from the group consisting of 1H-indole-3-methanol, ascorbigen, bis (3-indolyl) methane, [indolo[3,2-b(carbazole)]]indolo[3,2-b]carbazole, 2-(indol-3-ylmethyl)-3,3'-diindolylmethane, 5,6,11,12,17, 18-hexahydrocyclonona[1,2-b;4,5-b';7,8-b"]triindole, 1H-indol-3-yl methoxy methane, [ethoxy] 1H-indol-3-yl ethoxy methane, other ethers of 1H-indole-3-methanol, and mixtures of any thereof.

3. A method according to claim 2 wherein the 1H-indole-3-methanol compound is 1H-indole-3-methanol administered to the subject orally in an amount of from about 5 milligrams to about one gram daily.

4. A method according to claim 1 wherein the 1H-indole-3-methanol compound is administered in a single daily dose.

5. A method according to claim 1 wherein the 1H-indole-3-methanol compound comprises bis (3-indolyl) methane.

6. A method according to claim 1 wherein the 1H-indole-3-methanol compound comprises indolo[3,2-b]carbazole.

7. A method according to claim 1 wherein the 1H-indole-3-metbanol compound comprises 2-(indol-3-ylmethyl)-3,3'-diindolylmethane.

8. A method according to claim 1 wherein the 1H-indole-3-methanol compound comprises 5,6,11,12,17,18-hexahydrocyclonona[1,2-b;4,5-b';7, 8-b"]triindole.

9. A method according to claim 1 wherein the 1H-indole-3-methanol compound comprises ascorbigen.

10. A method according to claim 1 wherein the 1H-indole-3-methanol compound comprise 1H-indol-3-yl methoxy methane.

11. A method according to claim 1 wherein the 1H-indole-3-methanol compound comprises [ethoxy] 1H-indol-3-yl ethoxy methane, the ethyl ether of 1H-indole-3-methanol and/or other ethers of 1H-indole-3-methanol.

12. A method according to claim 1 wherein the 1H-indole-3-methanol compound comprises a mixture of dietary indoles, said dietary indoles selected from the group consisting of 1H-indole-3methanol; bis (3-indolyl) methane; indolo[3,2-b]carbazole; 2-(indol-3-ylmethyl)-3, 3'diindolylmethane; 5,6,11,12,17,18-hexahydrocyclonona [1,2-b;4,5-b';7,8-b"]triindole; ethers of 1H-indole-3-methanol; and ascorbigen.

13. A method according to claim 1 further comprising administering a dietary supplement containing a pharmaceutically acceptable amount of proanthocyanin in a pharmaceutically acceptable form to said subject each day the method is performed.

14. A method according to claim 1 further comprising administering a dietary supplement containing blue-green algae to said subject each day the method is performed.

15. A method according to claim 1 further comprising administering pharmaceutically effective amount of malic acid to said subject on a daily basis.

16. A method according to claim 1 further comprising administering pharmaceutically effective amount of a magnesium salt to said subject each day the method is performed.

17. A method of treating fibromyalgia syndrome in a subject believed to be suffering therefrom, said method comprising:

administering to the subject an estradiol 2-hydroxylase inducing compound in a medically acceptable manner in a pharmaceutically effective amount on a regular basis.

18. A method according to claim 17 wherein the estradiol 2-hydroxylase inducing compound is an 1H-indole-3-methanol compound.

19. A method according to claim 18 wherein the 1H-indole-3-methanol compound is 1H-indole-3-methanol.

20. A method according to claim 19 wherein the 1H-indole-3-methanol is administered, by mouth, in an amount of from about 200 to about 400 milligrams per day.

21. A method of treating fibromyalgia syndrome in a subject believed to be suffering therefrom, said method comprising:

orally administering to the subject an indole containing compound selected from the group consisting of 1H-indole-3-methanol, ascorbigen, bis (3-indolyl) methane, indolo[3,2-b]carbazole, 2-(indol-3-ylmethyl)-3,3'-diindolylmethane, 5,6,11,12,17,18-hexahydrocyclonona[1,2-b;4,5-b';7,8-b"]triindole, 1H-indol-3-yl methoxy methane, 1H-indol-3-yl ethoxy methane, other ethers of 1H-indole-3-methanol, and mixtures of any thereof in a dose of 5 to 1000 milligrams of the selected indole-containing compound daily in either single or divided doses.

* * * * *

UNITED STATES PATENT AND TRADEMARK OFFICE
CERTIFICATE OF CORRECTION

PATENT NO : 5,895,787
DATED : April 20, 1999
INVENTOR(S) : Arffmann et al.

It is certified that error appears in the above-identified patent and that said Letters Patent are hereby corrected as shown below:

On the title page:

In Item [56], "Other Publications", col. 1, line 21, change "Fibromyaigia" to --"Fibromyalgia--;

In Item [56], "Other Publications", col. 1, line 23, change "Fibromyaigia" to --"Fibromyalgia--; and In Item [56], "Other Publications", col. 2, line 5, after "What" insert --Have--.

In the specification:

| | | |
|---|---|---|
| Column 2, | line 17, | change "or" to --*for*--; |
| Column 3, | line 22, | change "indolo[2,3, -b(carbazole)]" to --indolo[2,3-b(carbazole)]--; |
| Column 3, | line 25 | change "hexahydrocyclohnona[1," to --hexahydrocyclonona[1,--; |
| Column 3, | line 26, | change "2-b;4,5-b';7,8-also" to --2-b;4,5-b';7,8-b"]triindole also--; |
| Column 3, | line 34, | change ""tH-indole-3-methanol" to --1*H*-indole-3-methanol--; |
| Column 5, | line 45, | change "1H-indole3-" to --1*H*-indole-3---; |
| Column 4, | line 29, | change "fig" to --filling--; |
| Column 5, | line 57, | change "EXAMPLE m" to --EXAMPLE III--; and |
| Column 6, | line 7, | change "what" to --What--. |

UNITED STATES PATENT AND TRADEMARK OFFICE
CERTIFICATE OF CORRECTION

PATENT NO : 5,895,787
DATED : April 20, 1999
INVENTOR(S) : Arffmann et al.

It is certified that error appears in the above-identified patent and that said Letters Patent are hereby corrected as shown below:

In the claims:

| | | | |
|---|---|---|---|
| Claim 2, | Column 6, | line 17, | after "methane," delete "[indolo[3,2-b(carbazole)]]"; |
| Claim 2, | Column 6, | line 20, | delete "[ethoxy]"; |
| Claim 11, | Column 6, | line 45, | after "comprises" delete "[ethoxy]"; |
| Claim 15, | Column 6, | line 65, | after "administering" insert --a--; and |
| Claim 16, | Column 6, | line 68, | after "administering" insert --a--. |

Signed and Sealed this

Eighth Day of May, 2001

NICHOLAS P. GODICI

*Attesting Officer*   Acting Director of the United States Patent and Trademark Office

*Attest:*